US006828309B2

(12) United States Patent
Striker (10) Patent No.: US 6,828,309 B2
(45) Date of Patent: Dec. 7, 2004

(54) USE OF PENTOSAN POLYSULFATE TO TREAT CERTAIN CONDITIONS OF THE PROSTATE

(75) Inventor: Gary E. Striker, Coral Gables, FL (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/209,331

(22) Filed: Jul. 30, 2002

(65) Prior Publication Data

US 2003/0040491 A1 Feb. 27, 2003

Related U.S. Application Data

(63) Continuation of application No. 09/766,245, filed on Jan. 19, 2001, now abandoned.
(60) Provisional application No. 60/177,083, filed on Jan. 19, 2000.

(51) Int. Cl.$^7$ ........................ A01N 43/04; A61K 31/715
(52) U.S. Cl. .......................... 514/54; 514/25; 536/17.2; 536/17.5; 536/18.7; 536/123.1; 536/124
(58) Field of Search .............................. 536/17.2, 17.5, 536/18.7, 123.1, 124; 514/25, 54

(56) References Cited

U.S. PATENT DOCUMENTS

| 5,605,938 A | 2/1997 | Roufa et al. |
| 5,643,892 A | 7/1997 | Striker et al. |
| 5,795,909 A | 8/1998 | Shashoua et al. |

FOREIGN PATENT DOCUMENTS

| WO | WO99/18961 | 4/1999 |

OTHER PUBLICATIONS

Kilgore et al. Journal of Pharmacology and Experimental Therapeutics, 1998, vol. 285, pp. 987–994.*
Boyle et al. Adult Urology 1996, vol. 48, pp. 398–405.*
Nickel, Infections in Urology (1999), vol. 26, pp. 737–751.*
Boyle, Peter, et al., "Prostate Volume Predicts Outcome of Treatment of Benign Prostatic Hyperplasia with Finasteride: Meta–Analysis of Randomized Clinical Trials," *Urology*, 48:398–405 (1996).
Carraro, J.C., et al., "Comparison of Phytotherapy (Permixon®) With Finasteride in the Treatment of Benign Prostate Hyperplasia: A Randomized International Study of 1,098 Patients," *The Prostate*, 29:231–240, (1996).
Coffey, Donald S., *Prostate Diseases*, 4$^{th}$ ed., "Chapter 4: The Molecular Biology of the Prostate," pp. 28–56, Philadelphia, W.B. Saunders Company (1993).

Gee, W.F., et al., "1997 American Urological Association Gallup Survey: Changes in Diagnosis and Management of Prostate Cancer and Benign Prostatic Hyperplasia, and Other Practice Trends From 1994 to 1997," *The Journal of Urology*, 160:1804–1807 (1998).
Hanno, P.M., "Analysis of Long–Term Elmiron Theraphy for Interstitial Cystitis," *Urology*, 49 (Suppl 5A):93–99 (1997).
Kilgore, K.S., et al., "The Semisynthetic Polysaccharide Pentosan Polysulfate Prevents Complement–Mediated Myocardial Injury in the Rabbit Perfused Heart," *The Journal of Pharmacological and Experimental Therapeutics*, 285(3):987–994 (1998).
Lush, R.M., et al., "A phase I study of pentosan polysulfate sodium in patients with advanced malignancies," *Ann. Oncol.*, 7:939–944 (1996).
Moore, E., et al., "Proscar®: Five–Year Experience," *Eur. Urol.*, 28:304–309 (1995).
Nickel, J.C., "Prostatitis: Evolving Management Strategies," *Infections in Urology*, 26(4):737–751 (1999).
Ryan, P.G. and Wallace, D.M.A., "Are We Making Progress in the Drug Treatment of Disorders of the Bladder, Prostate, and Penis?" *J. Clinical Pharmacy and Therapeutics*, 15:1–12 (1990).
Striker, G.E., et al., "Glomerulosclerosis, arteriosclerosis, and vascular graft stenosis: Treatment with oral heparinoids," *Kidney International*, 52(Suppl 63):S120–S123 (1997).
Wedrén, H., "Effects of Sodium Pentosanpolysulphate on Symptoms Related to Chronic Non–Bacterial Prostatitis," *Scand. J. Urol. Nephrol.*, 21:81–88 (1987).
Zenjari, C., et al., "Experimental evidence for FGF–1 control of blastema cell proliferation during limb regeneration of the Amphibian *Pleurodeles waltl*," *Int. J. Dev. Biol.*, 40:965–971 (1996).
Wedren, H., "Effects of Sodium Pentopolysulphate on Symptoms Related to Chronic Non–Bacterial Prostatitis," *Scand. J. Urol. Nephrol.*, 21:81–88, 1987.
Nickel, J.C., "Prostatitis: Evolving Management Strategies," *Urol. Clin. North Am.*, 26(4)737–751, Nov. 1999.

* cited by examiner

Primary Examiner—Elli Peselev
Assistant Examiner—Patrick T. Lewis
(74) *Attorney, Agent, or Firm*—Klarquist Sparkman, LLP (57) ABSTRACT

The invention relates to the field of pharmacology. More particularly, the invention relates to the treatment of prostate conditions, such as BPH. The invention provides new therapeutic compositions and methods for treating BPH, as well as chronic prostatitis, prostadynia, and irritative bladder conditions, other than interstitial cystitis. The compositions and methods according to the invention, which may be administered orally, efficaciously and safely treat the designated conditions by causing regression of established lesions and reduction of bladder irritation. In particular, the compositions and methods of the invention treat BPH by reducing the size of the prostate gland and decreasing the associated obstructive symptoms.

8 Claims, 5 Drawing Sheets

USE OF PENTOSAN POLYSULFATE TO TREAT CERTAIN CONDITIONS OF THE PROSTATE

PRIORITY CLAIM

This is a continuation of U.S. patent application Ser. No. 09/766,245 filed Jan. 19, 2001, now abandoned which claims the benefit of U.S. Provisional Application 60/177,083 filed Jan. 19, 2000.

BACKGROUND OF THE INVENTION

1. Field of the Invention

The invention relates to the field of pharmacology. More particularly, the invention relates to the treatment of prostate conditions, such as benign prostatic hyperplasia.

2. Summary of the Related Art

Benign prostatic hyperplasia (BPH) is a common disease. The advent of medical therapy for BPH has had a major impact on the practice of urologic care. Gee et al., JURL 160: 1804–1807 (1998), teaches that the overwhelming majority of American urologists use medical therapy first in patients with moderate symptoms.

Currently available medical therapy includes alpha blocking agents, 5-alpha-reductase inhibitors and phytotherapeutic agents. Five-alpha-reductase inhibitors block the conversion of testosterone to dihydrotestosterone (DHT) Moore et al., Euro URL 28: 304–309 (1995) teaches that finasteride, a type II 5-alpha-reductase-inhibitor, produced a 72% decrease in DHT, prostate volume reductions of 30% and a reduction in prostate specific antigen Boyle et al, Urology 48: 398–405 (1996) teaches that the symptomatic response to finasteride is greater in prostates weighing over 40 grams. Carraro et al., Prostate 29: 231–240 (1996) discloses that phytoestrogens provide improvements in uroflow, symptom scores and quality of life nearly equal to that provided by finasteride.

Thus, some progress has been made in noninvasive treatment for BPH. However, the underlying pathology in BPH involves proliferation of smooth muscle cells and increased deposition of extracellular matrix. Thus, there is a need for new treatments that can reduce or eliminate these two factors. Therefore, there remains a need for new therapeutic compositions and methods for treating BPH, as well as chronic prostatitis, prostadynia, and irritative bladder conditions, other than interstitial cystitis. Ideally, such compositions and methods should be orally administered, and should efficaciously and safely treat the designated conditions by causing regression of established lesions and reduction of bladder irritation. In particular, the compositions and methods should treat BPH by reducing the size of the prostate gland and decreasing the associated obstructive symptoms.

BRIEF SUMMARY OF THE INVENTION

The invention relates to the field of pharmacology. More particularly, the invention relates to the treatment of prostate conditions, such as BPH. The invention provides new therapeutic compositions and methods for treating BPH, as well as chronic prostatitis, prostadynia, and irritative bladder conditions, other than interstitial cystitis. The compositions and methods according to the invention reduce or eliminate both smooth muscle cell proliferation and extracellular matrix deposition. The compositions and methods according to the invention, which may be administered orally, efficaciously and safely treat the designated conditions by causing regression of established lesions and reduction of bladder irritation. In particular, the compositions and methods of the invention treat BPH by reducing the size of the prostate gland and decreasing the associated obstructive symptoms.

The present inventor has surprisingly discovered that pentosan polysulfate (PPS, commercially available as Elmiron® from Ivax Corp., Miami, Fla.) can cause regression of scarring and established and proliferative lesions of prostatic tissue.

In one aspect, the invention provides methods for treating prostate conditions. The methods according to the invention comprise administering to a mammal having a condition of the prostate selected from the group consisting of benign prostatic hyperplasia, chronic prostatitis, prostadynia, and an irritative bladder condition, which is other than interstitial cystitis, a treatment effective amount of pentosan polysulfate or a pharmaceutically acceptable salt thereof.

In certain preferred embodiments, the condition of the prostate is benign prostatic hyperplasia. In certain preferred embodiments, the pentosan polysulfate or pharmaceutically acceptable salt thereof is administered orally. In certain preferred embodiments, the treatment effective amount is from about 5 mg/kg to about 30 mg/kg of body weight per day.

DETAILED DESCRIPTION OF THE PREFERRED EMBODIMENTS

The invention relates to the field of pharmacology. More particularly, the invention relates to the treatment of prostate conditions, such as BPH. The patents and publications cited in this specification evidence the knowledge in this field and are hereby incorporated by reference in their entirety. In the case of conflict between any teaching of a reference cited in this specification and any teaching specifically disclosed in this specification, the teaching specifically disclosed in this specification shall prevail.

The invention provides new therapeutic compositions and methods for treating BPH, as well as chronic prostatitis, prostadynia, and irritative bladder conditions, other than interstitial cystitis. The compositions and methods according to the invention reduce or eliminate both smooth muscle cell proliferation and extracellular matrix deposition. The compositions and methods according to the invention, which may be administered orally, efficaciously and safely treat the designated conditions by causing regression of established lesions and reduction of bladder irritation. In particular, the compositions and methods of the invention treat BPH by reducing the size of the prostate gland and decreasing the associated obstructive symptoms.

The present inventor has surprisingly discovered that pentosan polysulfate (PPS; commercially available as Elmiron® from Ivax Corp., Miami, Fla.) can cause regression of scarring and established and proliferative lesions of prostatic tissue. Coffey et al., *Prostate Diseases*, 4$^{th}$ ed., pp. 28–56 (Philadelphia, 1993), teach that prostate growth is modulated by endocrine, neuroendocrine, paracrine, autocrine, intracrine, and extracellular matrix factors, and cell-cell interactions. PPS affects mainly extracellular matrix regulation, but may also inhibit complement activation, antagonize growth factor binding, and inhibit DNAse activity, among other effects. See Kilgore et al., J. Pharmacol. Exp. Ther. 285:987–94 (1998); Lush et al., Ann. Oncol. 7:939–44 (1996); Zenjari et al., Int. J. Dev. Biol. 40:965–71 (1996)). PPS has been studied for 30 years and has been approved by the U.S. Food and Drug Administration for the treatment of interstitial cystitis (IC) as Elmiron® (Ivax Corp., Miami, Fla.) PPS is advantageous because it is associated with a very low incidence of side effects. Sand et alt, Urology, 49(Suppl. 5A):93–99 (1997) disclose that serious adverse effects in patients treated for IC were mainly gastrointestinal or alopecia in 3.2% of chronic users.

In one aspect, the invention provides methods for treating prostate conditions. The methods according to the invention comprise administering to a mammal having a condition of the prostate selected from the group consisting of benign prostatic hyperplasia, chronic prostatitis, prostadynia, and an irritative bladder condition, which is other than interstitial cystitis, a treatment effective amount of pentosan polysulfate or a pharmaceutically acceptable salt thereof. In certain preferred embodiments, the condition of the prostate is benign prostatic hyperplasia.

For purposes of the inventions the term "mammal" is used in its usual taxonomic sense and specifically includes humans.

For purposes of the invention, the term "pharmaceutically acceptable" is used in its usual sense within the industry.

As used herein, the term "treatment effective amount" refers to an amount that is effective, when given one or more times daily for a prescribed period of lime, in causing the regression of scarring and established and proliferative lesions and the reduction of bladder irritation symptoms associated with BPH, chronic prostatitis, prostadynia, and irritative bladder conditions other than interstitial cystitis. One skilled in the art will recognize that the amount will depend upon a variety of factors including species, age, body weight, condition or disease state, and amount of the prostate affected by the condition. The treatment effective amount will also depend on the route and timing of administration, the existence, nature, and extent of any adverse side effects, and the desired physiological effect. It will be appreciated by one of ordinary skill in the art that various conditions or disease states, in particular, chronic conditions or disease states, may require prolonged treatment involving multiple administrations.

Suitable doses and dosage regimens may be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached.

In certain preferred embodiments, the treatment effective amount is from about 5 mg/kg to about 30 mg/kg of body weight per day. Preferably, a dosage unit comprises from about 50 mg to about 500 mg of PPS or a pharmaceutically acceptable salt thereof. In smaller mammals, the dosage range may have to be adjusted downward in accordance with species, body weight, and nature of the condition.

In certain preferred embodiments, PPS, or a pharmaceutically acceptable salt thereof is administered as soon as possible after BPH, chronic prostatitis, prostadynia or an irritative bladder condition other than interstitial cystitis is diagnosed. In other preferred embodiments, PPS, or a pharmaceutically acceptable salt thereof, is administered as soon as possible after a mammal, such as a human, is determined to be at risk of developing BPH, chronic prostatitis, prostadynia or an irritative bladder condition other than interstitial cystitis.

PPS is a highly sulfated semi-synthetic polysaccharide, which has a molecular weight ranging from about 1,500 Daltons to about 6,000 Daltons, depending on the mode of isolation. PPS is a macromolecular carbohydrate derivative, which chemically and structually resembles glycosaminoglycans. The polysaccharide backbone of PPS, xylan, may conveniently be extracted from tree bark, e.g., from the bark of the beechwood tree or purchased commercially (Sigma, St. Louis, Mo.) and treated with a sulfating agent, such as, but not limited to chlorosulfonic acid or sulfuryl trichloride and acid. After sulfation, PPS is usually treated with sodium hydroxide to yield the sodium salt.

PPS may be formulated as a pharmaceutically acceptable acid additions salt. Nonlimiting examples of pharmaceutically acceptable acid addition salts for use in the present invention include those derived from mineral acids, such as, but not limited to, hydrochloric, hydrobromic, phosphoric, metaphosphoric, nitric and sulfuric acids; and organic acids, such as, but not limited to, tartaric, acetic, citric, malic, lactic, furnaric, benzoic, glycolic, gluconic, succinic, and arylsulphonic, such as, but not limited to, p-toulenesulphonic acid.

Pharmaceutical compositions for use in the methods of the present invention preferably comprise a pharmaceutically acceptable carrier and an amount of PPS, or a pharmaceutically acceptable salt thereof, sufficient to treat BPH, chronic prostatitis, prostadynia or an irritative bladder condition, other than interstitial cystitis, prophylactically and/or therapeutically. The carrier may be any of those conventionally used in the art. Choice of carrier is limited only by chemico-physical considerations, such as solubility and lack of reactivity with the compound, and by the route of administration. Preferably, the pharmaceutically acceptable carrier is chemically inert to PPS, or a pharmaceutically acceptable salt thereof and has no detrimental side effects or toxicity under the conditions of use. It will be appreciated by one of skill in the art that there are a wide variety of suitable formulations of the pharmaceutical compositions of the present invention. For example, in addition to the following described pharmaceutical compositions, PPS, or a pharmaceutically acceptable salt thereof, may be formulated as inclusion complexes, such as, but not limited to, cyclodextrin inclusion complexes, or as liposomes.

The pharmaceutically acceptable excipients described herein, including vehicles adjuvants, carriers, and diluents, are well-known to those who are skilled in the art and are readily available to the public. The choice of excipient will be determined in part by the particular method used to administer the composition. One skilled in the art will appreciate that multiple suitable methods of administering PPS, or a pharmaceutically acceptable salt thereof, in the method of the present invention are available. Nonlimiting examples of possible routes for administration include oral, parenteral, subcutaneous, intravenous, intramuscular, and interperitoneal. Although more than one route may be used to administer PPS, or a pharmaceutically acceptable salt thereof, a particular route may provide a more immediate or more effective reaction than another route. The following described methods and formulations for administration are merely exemplary and are in no way limiting.

In some preferred embodiments, the PPS or pharmaceutically acceptable salt thereof is administered orally. Formulations suitable for oral administration include, without limitation, liquid solutions and suspensions, emulsions, powders, and solid formulations. Liquid solutions and suspensions comprise a therapeutically effective amount of the compound dissolved or suspended in a liquid, such as, but not limited to, water, saline, or orange juice. Liquid formulations may include diluents, such as, but not limited to, water and alcohols, such as, but not limited to, ethanol, benzyl alcohol, and polyethylene alcohols. Liquid formulations may also include a pharmaceutically acceptable surfactant, suspending agent, or emulsifying agent.

Solid formulations suitable for oral administration according to the methods of the present invention include capsules, sachets, tablets, lozenges, and troches, each containing a predetermined amount of the active ingredient as solids or granules. Capsules may be of the ordinary hard- or soft-shelled gelatin type and may contain, without limitation, surfactants, lubricants, and inert fillers, such as, but not limited to, lactose, sucrose, calcium phosphate, and corn starch. Tablets may include, without limitation, one or more of lactose, sucrose, mannitol, corn starch, potato starch, alginic acid, microcrystalline cellulose, acacia gelatin, guar gum, colloidal silicon dioxide, croscarmellose sodium, talc, magnesium stearate, calcium stearate, zinc stearate, stearic acid and other colorants, diluents, buffering agents, disintegrating agents, moistening agents, preservatives, flavoring agents, and pharmacologically compatible excipients. Lozenges preferably comprise the active ingredient in a flavor, preferably sucrose and acacia or tragacanth, as well as pastilles comprising the active ingredient in an inert base, such as, but not limited to, gelatin and glycerin, or sucrose and acacia, emulsions, gels, and the like, containing, in addition to the active ingredient, such excipients as are known in the art. In a certain preferred embodiment, the oral dosage form is Elmiron® gelatin capsules (Baker Norton Pharmaceuticals, Inc. Miami, Fla.), which contain 100 mg of PPS sodium and, as excipients, microcrystalline cellulose and magnesium stearate.

In some preferred embodiments, the PPS or pharmaceutically acceptable salt thereof is administered parenterally. Preferably, injectable compositions are administered intravenously or locally, i.e., at or near the site of the prostate. The requirements for effective pharmaceutical carriers for injectable compositions are well known to those of ordinary skill in the art. See *Pharmaceutics and Pharmacy Practice*, pp. 238–50 (Banker and Chalmers, Eds, J. B. Lippincott Co. Philadelphia, 1982); *ASHP Handbook on Injectable Drugs*, $4^{th}$ ed, pp 622–30, Toissel, 1986).

Preferred parenteral formulations comprise from about 0.5% to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12% to about 15% by weight. Suitable surfactants include, without limitation, polyethylene sorbitan fatty acid esters, such as sorbitan monooleate, and high molecular weight adducts of ethylene oxide with a hydrophobic base, formed by the condensation of propylene oxide with propylene glycol. Parenteral formulations may be presented in unit-dose or multi-dose sealed containers, such as, but not limited to, ampules and vials, and may be stored in a freeze-dried (lyophilized) condition requiring only the addition of a sterile liquid excipient, such as, but not limited to, water, immediately prior to injection. Extemporaneous injection solutions and suspensions may be prepared from sterile powders, granules, and tablets of the kind previously described.

In some preferred embodiments, formulations suitable for parenteral administration are aqueous and non-aqueous isotonic sterile injection solutions, which may include, without limitation, anti-oxidants, buffers, bacteriostats, and solutes that render the formulations isotonic with the blood of the intended recipient. In other preferred embodiments, formulations suitable for parenteral administration are aqueous and non-aqueous sterile suspensions that may include, without limitation, suspending agents, solubilizers; thickening agents, stabilizers, and preservatives.

PPS or a pharmaceutically acceptable salt thereof may be administered parenterally in a physiologically acceptable diluent in a pharmaceutical carrier. Such formulations may comprise a sterile liquid or mixture of liquids, including, without limitation, water saline; aqueous dextrose and related sugar solutions; alcohols, such as, but not limited to, ethanol, isopropanol, and hexadecyl alcohol; glycols, such as, but not limited to, propylene glycol and polyethylene glycol: dimethylsulfoxide; glycerol ketals, such as, but not limited to, 2,2-dimethyl-1,3-dioxolane-4-methanol; others, such as, but not limited to, poly(ethyleneglycol) 400; an oil; a fatty acid; a fatty acid ester or glyceride; or an acetylated fatty acid glyceride; with or without a pharmaceutically acceptable surfactant, such as, but not limited to, a soap or a detergent; a suspending agent, such as, but not limited to, pectin, carbomers, methylcellulose, hydroxypropylmethylcellulose, or carboxymethylcellulose; or emulsifying agents and other pharmaceutical adjuvants.

Suitable types of oils for use in parenteral formulations include, without limitation, petroleum, animal vegetable, and synthetic oils. Suitable oils include, without limitation, peanut, soybean, sesame, cottonseed, corn, olive, petrolatum, and mineral oils. Suitable fatty acids for use in parenteral formulations include, without limitation, oleic acid, stearic acid, and isostearic acid. Ethyl oleate and isopropyl myristate are nonlimiting examples of suitable fatty acid esters. Suitable soaps for use in parenteral formulations include, without limitation, fatty alkali metals, ammonium, and triethanolamine salts. Suitable detergents include, without limitation, cationic detergents such as, but not limited to, dimethyl dialkyl ammonium halides and alkyl pyridinium halides; anionic detergents such as, but not limited to, alkyl, aryl, and olefin sulfonates, alkyl, olefin, ether, and monoglyceride sulfates, and sulfosuccinates, nonionic detergents such as, but not limited to, fatty amine oxides, fatty acid alkanolamides, and polyoxyethylenepolypropylene copolymers; amphoteric detergents such as, but not limited to, allyl-Ǝ-aminopropionates and 2-alkylimidazoline quaternary ammonium salts; and mixtures thereof.

The present inventive method also may involve the co-administration of other pharmaceutically active compounds. As used herein, "co-administration" means administration before, during, or after administration of PPS or a pharmaceutically acceptable salt thereof as described above.

In view of the above, PPS or a pharmaceutically acceptable salt thereof may also be administered to cells or tissues obtained from a prostate in the research and development of new treatment modalities of BPH, chronic prostatitis, prostadynia or an irritative bladder condition other than interstitial cystitis.

The following examples are provided to further illustrate certain preferred embodiments of the invention and are not intended in any way to limit the scope of the invention. The following examples collectively demonstrate that by decreasing the proliferation of prostatic smooth muscle cells and the amount of scar tissue, PPS, or a pharmaceutically acceptable salt thereof, can cause regression of scarring and established and proliferative lesions of prostatic tissue.

EXAMPLE 1

Cell Morphology & Cell Turnover

This example demonstrates that PPS inhibits prostatic smooth muscle cell proliferation without a concomitant increase in apoptosis.

Figure 1:
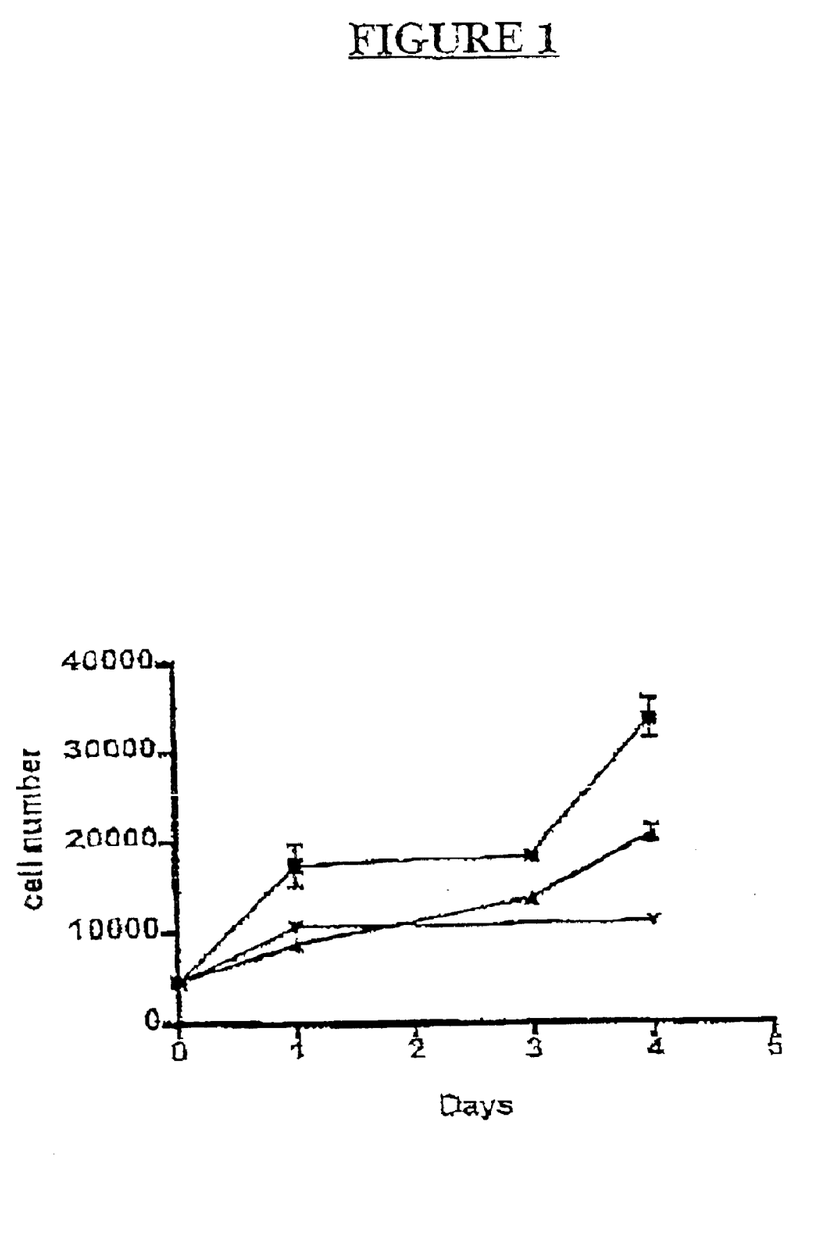
FIG. 1 shows levels of alpha smooth muscle cell actin in smooth muscle cells.
Figure 2:
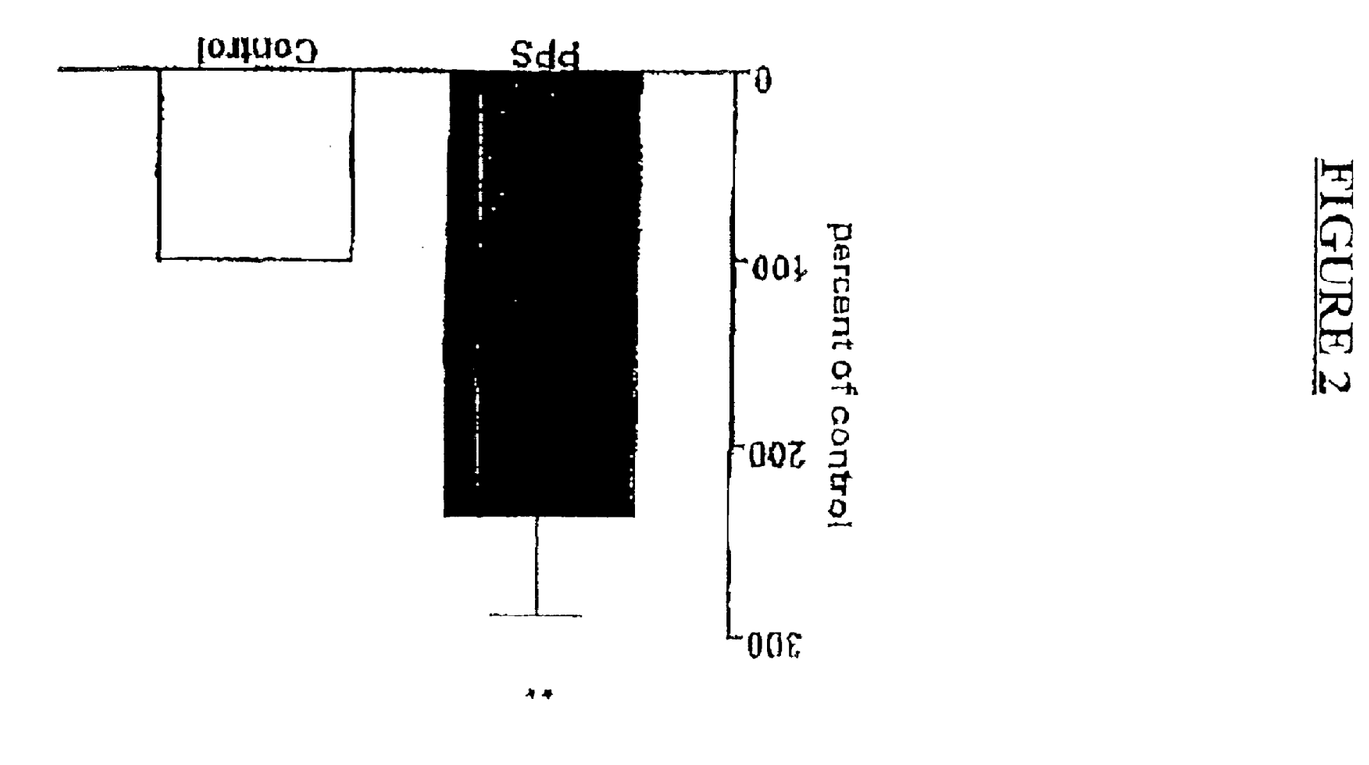
FIG. 2 shows growth curves for human prostate cells plated in 20% serum containing medium. Following a 24 hour attachment, pentosan polysulfate (10 μg/ml ▩ or 100 μg/ml Δ) was added to appropriate wells. Duplicate wells were counted on days 1, 3 and 4.

Fragments from the nodular areas of prostatectomy specimens were obtained, cut into small pieces, and incubated in a collagenase solution (3 mg/ml) (Sigma Chemical Co., St. Louis, Mo.) overnight at 37° C. The following day, the digested fragments were resuspended in complete Waymouth's medium (Gibco) containing 20% fetal bovine serum (FBS), L-glutamine, penicillin (100 U/ml), streptomycin (100 $\mu$g/ml), and sodium bicarbonate. The digested fragments were then plated into 24-well plates (Nunc Nalge International, Naperville, Ill.) coated with human fibronectin (Collaborative Research). The fragments were left undisturbed in 95% $O_2$ and 5% $CO_2$ until the first outgrowth was apparent (by day 7), at which time the cells appeared elongated and stellate and formed parallel arrays. The medium was changed twice a week until the cells reached confluence, at which time the cells were transferred into flasks. All experiments were performed on cells between passage 2 and 10, at which time the cells appeared to have a stable phenotype (i.e., monolayer growth with no morphological change and no hillock formation at confluence). Characterization was performed by staining for a smooth muscle cell actin (Sigma Chemical Co.) and F actin (Molecular Probes) in accordance with manufacturers' directions. All of the cells contained end to end actin filaments when stained with phalloidin. Such staining is characteristic of mesenchymal cells. Since the majority of the cells contained smooth muscle actin (see FIG. 1), the cells were considered to be smooth muscle cells Dose response curves for the cells were generated by plating cells at 5,000 cells/well in 24-well plates (Nunc) in medium containing 20% FBS. After 36 hours, the medium was replaced with fresh 20% FBS containing medium and increasing concentrations of PPS (Elmiron®, Ivax Corp., Miami Fla.) were added. Cells were counted on days 1, 3 and 4 with a Coulter 7.1 cell counter (Coulter, Hialeah, Fla.). The addition of FBS stimulated cell proliferation. There was no change in the growth rate in the 10 passages studied and cell proliferation was markedly inhibited at confluence. Cell number decreased 24 hours following treatment with PPS (10 or 100 $\mu$g/ml) (see FIG. 2). This was not associated with cell death, as assessed by trypan blue staining. Cell number decreased by 3-fold by day 4 of treatment with 100 $\mu$g/ml PPS.

EXAMPLE 2

Zymography for Metalloproteinases

This example demonstrates that PPS does not affect matrix metalloproteinase activity.

Cells in medium containing 20% FBS were pipetted into 6-well plates and were left undisturbed for 24 hours. On day 0, fresh medium containing 20% serum, with and without PPS (100 $\mu$g/$\mu$l), was added PPS was added daily for 5 days. At day 4, the serum in the medium was reduced to 0.1% FBS so as to avoid interference with the assays. At the time of collection, the cellular supernatants were centrifuged to remove cellular debris. Cell layers from the same wells were used to determine cell number.

Figure 3:
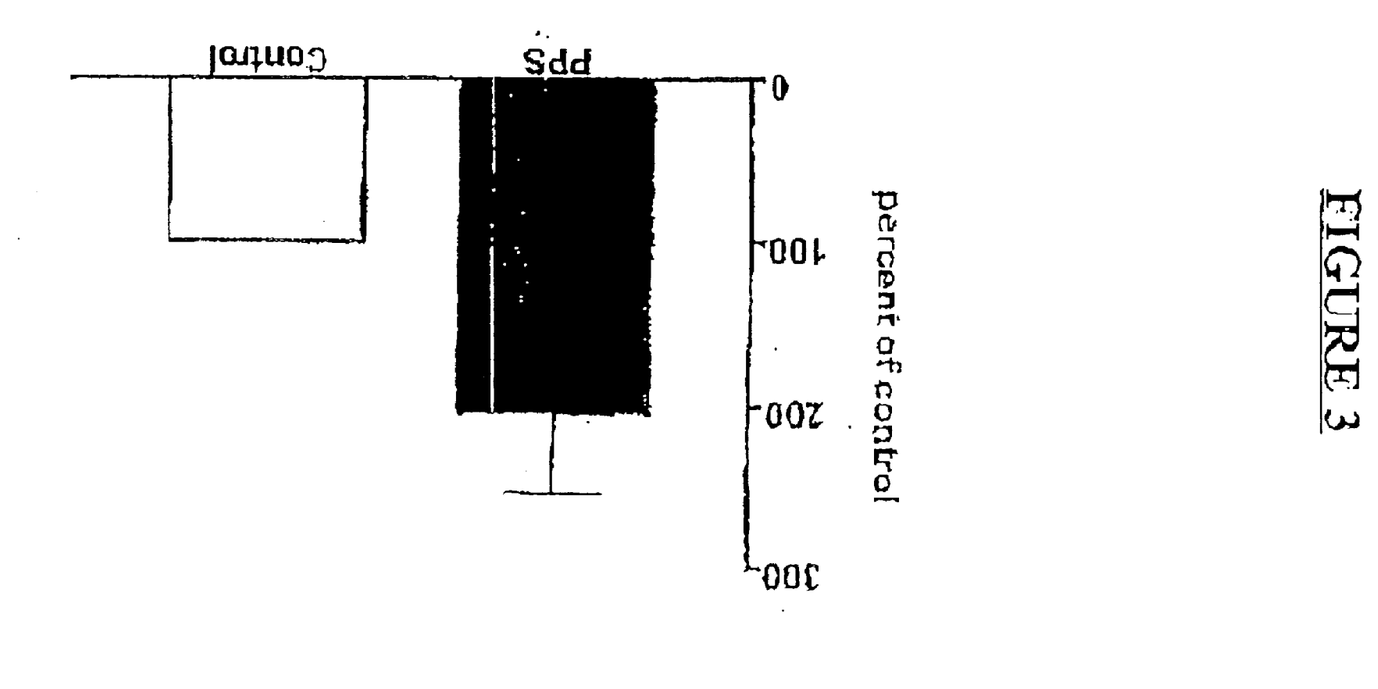
FIG. 3 shows increased MMP-9 activity in pentosan polysulfate treated cells as a percent of untreated control cells (p<0.001).
Figure 4:
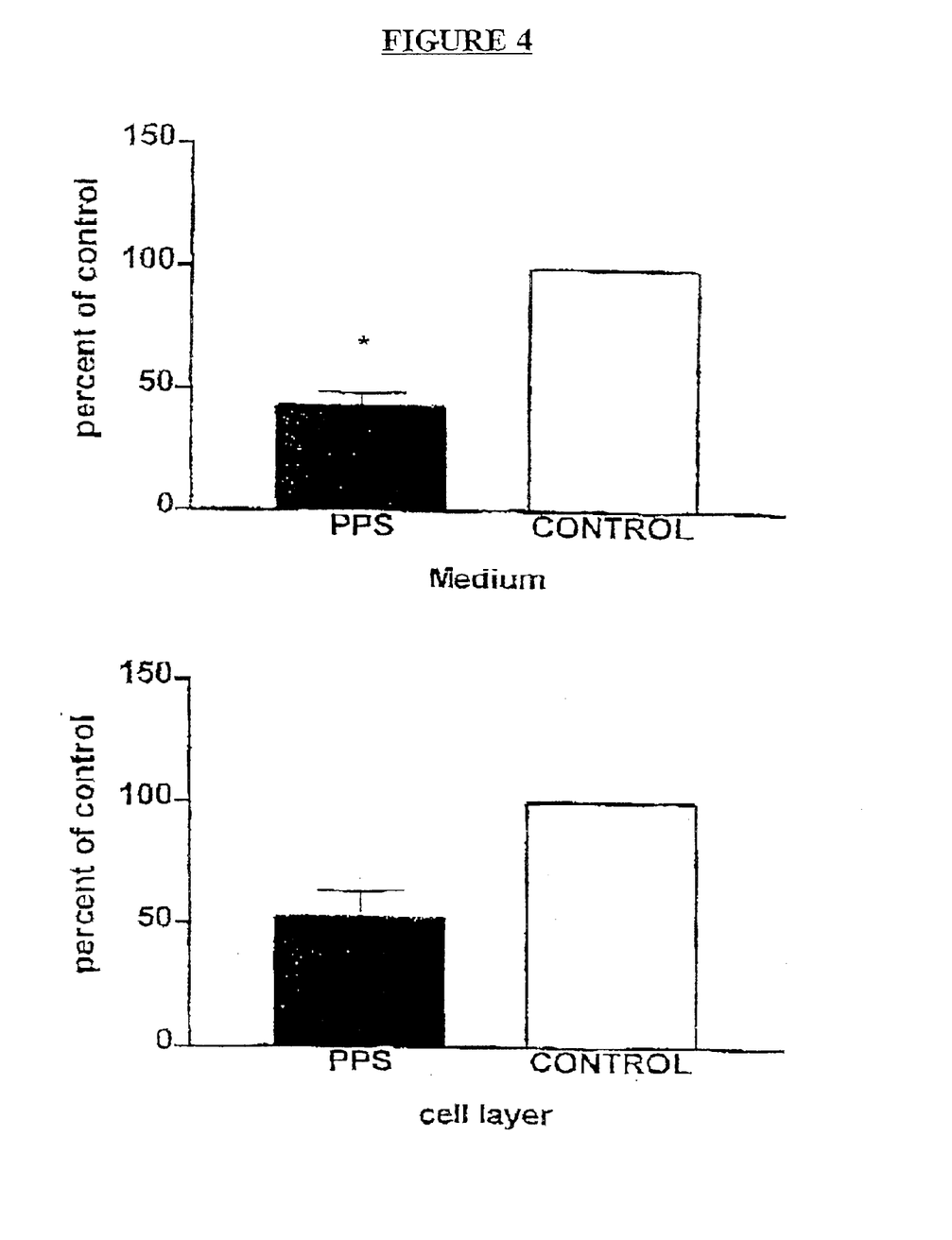
FIG. 4 shows increase in TIMP-1 cells treated with pentosan polysulfate as a percent of untreated control cells.

Briefly, medium was diluted with 0.1% FBS and 5× Laemmli buffer so that all samples corresponded to an identical cell number. Gelatinases (MMP-9 and MMP-2) in the medium were assayed using 10% zymogram gels (Novex, San Diego, Calif.). Following electrophoresis, the gels were washed for 1 hour in 2.5% SDS and incubated overnight in collagenase as described previously (Boyle et al., Urology 48: 398–405, 1996). The gels were stained with Coomassie Blue and air-dried. To check for non-specific bands, gels were incubated in 50 mM Tris buffer, with the addition of 25 mM EDTA. Quantitative densitometry was performed using NIH image 1.6. There were no significant differences in MMP-2 levels between PPS-treated cells and control cells. However MMP-9 increased 235.7+/−50.31 as compared to control cells (see FIG. 3) (p<001).

EXAMPLE 3

Reverse Zymography

This example demonstrates that PPS increases the amount of tissue inhibitor of metalloproteinase 1 activity.

Tissue inhibitors of metalloproteinases (TIMPS) in the supernatant and the cell layer were assessed by reverse zymography. Briefly, gels were prepared containing gelatinase A. Medium was diluted to normalize for cell number as described in Example 2. Gels were washed for 1 hour in 2.5% SDS following electrophoresis and incubated overnight at 37° C. Coomasie Blue staining and air drying was performed as described in Example 2. Densitometry was performed using NIH image 1.6 to quantitate the TIMPS activity.

TIMP-1 and TIMP-2 were present in the media of the isolates examined. In those cells treated with PPS, TIMP-1 levels were increased 203.5+/−50.31 as compared to control cells in contrast, TIMP-2 was expressed at high levels in the medium of all cells treated with PPS and was barely detectable in the control medium.

EXAMPLE 4

Collagen Analysis

This example demonstrates that PPS reduces the synthesis of type I and type IV collagen.

Another set of cells was plated as described in Example 2 and either treated with PPS or left untreated. The supernatant was centrifuged to remove cellular debris and transferred to a tube containing protease inhibitors (PMSF, NEM, EDTA) and frozen prior to assay.

Type I collagen: 100 $\mu$l of medium or human collagen type I standard were incubated for 24 hours in a 96 well plate (Nunc). After 3 washes with 0.05% Tween/PBS, the wells were blocked with 1% BSA/PBS for an additional 24 hours. Following 4 washes with 0.05% Tween/PBS, 50 µl of human collagen type I antibody (1:1000) (Biodesiga, Kennebunk, Me.) was applied for 90 minutes. The plate was washed again and biotin-labeled goat anti-rabbit IgG (1:1000, Sigma) was applied for 1 hour. The wells were washed 4 more times and incubated with streptavidin horseradish peroxidase (SAAP) at a 1:2500 concentration. P-nitrophenyl phosphate (pNPP, Sigma) was used for color development according to the manufacturer's directions. The plate was read in a Titertek Mulitskan plate reader at 405 nm.

Type IV collagen: The Assay was performed in a similar way, except the medium and standards were coated on the plate for 8 hours prior to blocking. The concentration of the antibody and the biotinylated goat anti-rabbit IgG was 1:2000. The SAAP was used at 1:1500.

Type I and type IV (Biodesign) collagen standards were diluted to a final concentration of 0.25–4 ng/well in 0.02 N acetic acid. The curves were linear (r=0.98).

Figure 5:
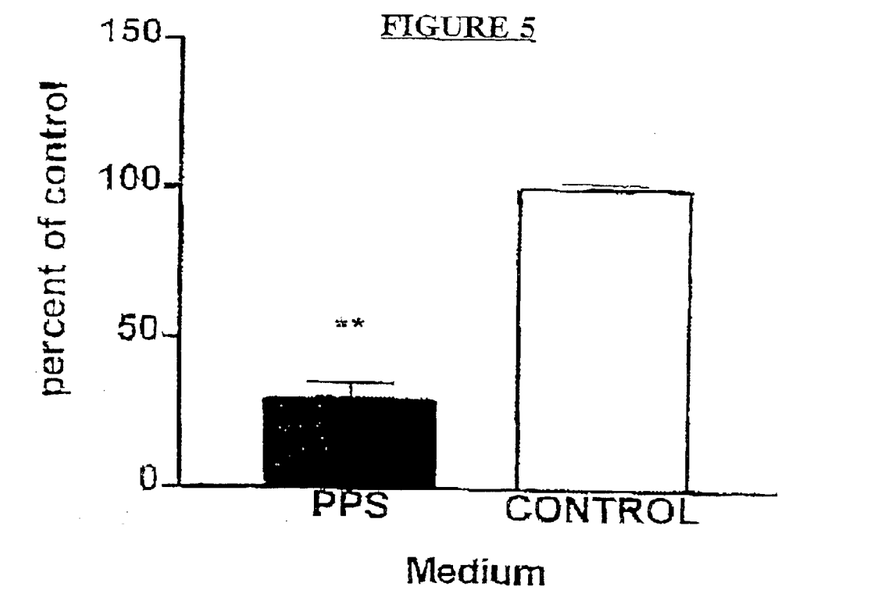
FIG. 5 shows reduction in ▩ type (IV) synthesis in pentosan polysulfate treated cells (black bar) compared to untreated control cells (open bar). (p<0.05).
Figure 6:
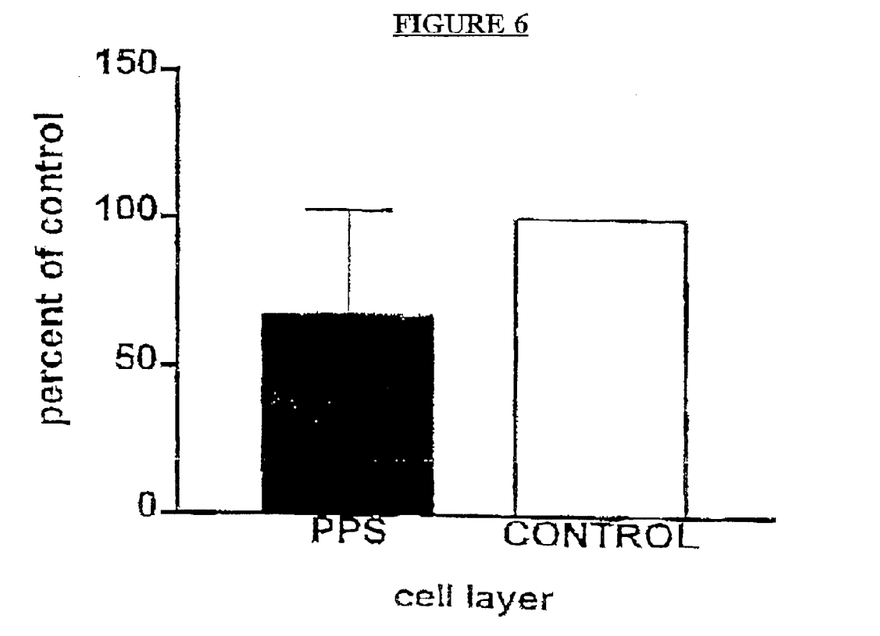
FIG. 6 shows reduction in ▩ type (I) synthesis in pentosan polysulfate treated cells (black bar) compared to untreated control cells (open bar). (p<0.005).

The cells produced types I and IV collagen. The cells treated with PPS showed a decrease of type IV collagen in the medium (43.03%+/−4.029%, $p<0.05$) and cell layer (52.99%+/−7.556%, $p<0.05$) in comparison to untreated cells (see FIG. 5). Similarly, there was a decrease in type I collagen in the medium (29.97%+/−3.692%, $p<0.005$) and cell layer (66.91%+/−25.42%) (values expressed as % of controls) (see FIG. 6).

While the foregoing invention has been described in some detail for purposes of clarity and understanding, it will be appreciated by one skilled in the art from a reading of this disclosure that various changes in form and detail may be made without departing from the scope of the invention and the attached claims.

What is claimed is:

1. A method for treating benign prostatic hyperplasia comprising administering to a mammal having benign prostatic hyperplasia, a treatment effective amount of pentosan polysulfate or a pharmaceutically acceptable salt thereof.

2. The method of claim 1, wherein the pentosan polysulfate or pharmaceutically acceptable salt thereof is administered orally.

3. The method of claim 1, wherein the treatment effective amount is from about 5 mg/kg to about 30 mg/kg of body weight per day.

4. The method of claim 1, wherein the method of treatment reduces prostate size.

5. A method for treating a mammal at risk for benign prostatic hyperplasia, comprising administering a treatment effective amount of pentosan polysulfate or a pharmaceutically acceptable salt thereof to a mammal at risk for benign prostatic hyperplasia.

6. The method of claim 5, wherein the pentosan polysulfate or pharmaceutically acceptable salt thereof is administered orally.

7. The method of claim 5, wherein the treatment effective amount is from about 5 mg/kg to about 30 mg/kg of body weight per day.

8. The method of claim 5, wherein the method of treatment inhibits prostatic smooth muscle cell proliferation.

* * * * *

UNITED STATES PATENT AND TRADEMARK OFFICE
CERTIFICATE OF CORRECTION

PATENT NO. : 6,828,309 B2
DATED : December 7, 2004
INVENTOR(S) : Striker

It is certified that error appears in the above-identified patent and that said Letters Patent is hereby corrected as shown below:

Column 3,
Line 23, "Fla.) PPS" should read -- FL). PPS --
Line 24, "alt, Urology," should read -- al., Urology --

Column 5,
Lines 35-36, "acacia gelatin," should read -- acacia, gelatin --

Column 6,
Line 23, "solubilizers; thickening" should read -- solubilizers, thickening --
Line 33, "glycol: dimethylsulfoxide" should read -- glycol; dimethylsufoxide --
Line 56, "sulfosuccinates, non-" should read -- sulfosuccinates; non- --
Line 62, " allyl-" should read -- alkyl- --

Column 7,
Line 45, "staining for a smooth" should read -- staining for α smooth --
Line 52, "muscle cells" should read -- muscle cells. --
Line 59, "Miami Fla.)" should read -- Miami, FL) --

Column 8,
Line 9, "was added PPS" should read -- was added. PPS --
Line 29, "However MMP-9" should read -- However, MMP-9 --
Line 51, "cells in contrast," should read -- cells. In contrast, --

Column 9,
Line 3, "(Biodesiga," should read -- (Biodesign, --

Signed and Sealed this

Twenty-fourth Day of May, 2005

JON W. DUDAS
*Director of the United States Patent and Trademark Office*